United States Patent
Masunishi et al.

(10) Patent No.: US 9,952,112 B2
(45) Date of Patent: Apr. 24, 2018

(54) PRESSURE SENSOR, MICROPHONE, ULTRASONIC SENSOR, BLOOD PRESSURE SENSOR, AND TOUCH PANEL

(71) Applicant: KABUSHIKI KAISHA TOSHIBA, Tokyo (JP)

(72) Inventors: Kei Masunishi, Kanagawa (JP); Hideaki Fukuzawa, Kanagawa (JP); Yoshihiko Fuji, Kanagawa (JP); Akiko Yuzawa, Kanagawa (JP); Kazuaki Okamoto, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 31 days.

(21) Appl. No.: 14/721,523

(22) Filed: May 26, 2015

(65) Prior Publication Data
US 2015/0338300 A1    Nov. 26, 2015

(30) Foreign Application Priority Data
May 26, 2014   (JP) .................................. 2014-108501

(51) Int. Cl.
*G01L 9/16*     (2006.01)
*A61B 5/021*    (2006.01)

(52) U.S. Cl.
CPC ............ *G01L 9/16* (2013.01); *A61B 5/02141* (2013.01); *A61B 2562/028* (2013.01); *A61B 2562/0247* (2013.01); *A61B 2562/12* (2013.01)

(58) Field of Classification Search
CPC  G01L 9/16; A61B 5/02142; A61B 2532/0247
(Continued)

(56) References Cited

U.S. PATENT DOCUMENTS

| 6,694,822 B1 * | 2/2004 | Ganapathi | G01L 1/125 73/728 |
| 2003/0079549 A1 * | 5/2003 | Lokhorst | G01L 1/205 73/754 |

(Continued)

FOREIGN PATENT DOCUMENTS

| EP | 1939599 A2 | 7/2008 |
| JP | 56-114378 | 9/1981 |

(Continued)

OTHER PUBLICATIONS

Patrick R. Scheeper; et al.; "The Design, Fabrication, and Testing of Corrugated Silicon Nitride Diaphragms", Journal of Microelectromechanical Systems, vol. 3, No. 1, pp. 36-42, (1994).

(Continued)

*Primary Examiner* — John Chapman, Jr.
*Assistant Examiner* — Tarun Sinha
(74) *Attorney, Agent, or Firm* — Finnegan, Henderson, Farabow, Garrett & Dunner, L.L.P.

(57) ABSTRACT

According to an embodiment, a pressure sensor includes a support part, a flexible membrane part, and a magnetoresistive element. The flexible membrane part is supported by the support part, and includes a first region and a second region with rigidity lower than rigidity of the first region. The magnetoresistive element is provided on the membrane part, and includes a first magnetic layer, a second magnetic layer, and a spacer layer provided between the first magnetic layer and the second magnetic layer.

16 Claims, 9 Drawing Sheets

(58) Field of Classification Search
USPC .......................................................... 73/725
See application file for complete search history.

(56) References Cited

U.S. PATENT DOCUMENTS

| | | | |
|---|---|---|---|
| 2007/0186666 A1* | 8/2007 | Ruehrig | G01L 9/16 73/779 |
| 2008/0094059 A1 | 4/2008 | Sasaki et al. | |
| 2012/0055257 A1* | 3/2012 | Shaw-Klein | H01L 41/081 73/780 |
| 2013/0118265 A1* | 5/2013 | Besling | G01L 9/0042 73/724 |
| 2014/0069200 A1* | 3/2014 | Yuasa | G01L 9/16 73/725 |
| 2014/0369530 A1 | 12/2014 | Fuji et al. | |

FOREIGN PATENT DOCUMENTS

| | | |
|---|---|---|
| JP | 8-114408 | 5/1996 |
| JP | 8-247874 | 9/1996 |
| JP | 2008-107302 | 5/2008 |
| JP | 2009-41951 | 2/2009 |
| JP | 2009-198337 | 9/2009 |
| JP | 2011-247897 | 12/2011 |
| JP | 2014-52360 | 3/2014 |
| JP | 2014-240824 | 12/2014 |
| TW | 201323845 A1 | 6/2013 |

OTHER PUBLICATIONS

Office Action issued by the Taiwanese Patent Office in corresponding Taiwanese Patent Application No. 104116488, dated Mar. 10, 2016, and an English-language translation of the Office Action (11 pages).

* cited by examiner

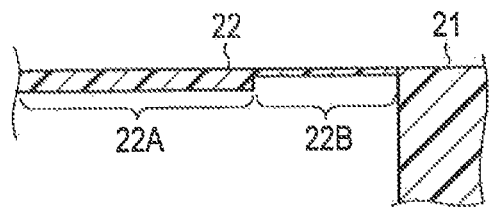
F I G. 4A
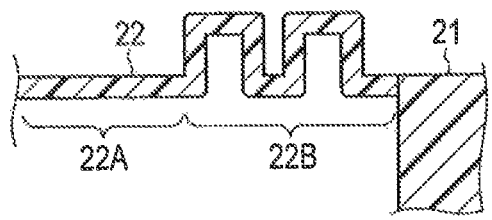
F I G. 4B
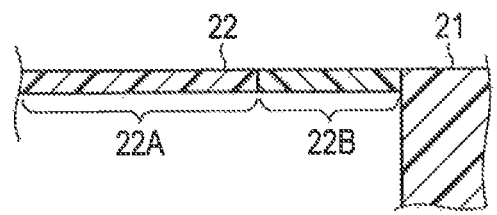
F I G. 4C

PRESSURE SENSOR, MICROPHONE, ULTRASONIC SENSOR, BLOOD PRESSURE SENSOR, AND TOUCH PANEL

CROSS-REFERENCE TO RELATED APPLICATIONS

This application is based upon and claims the benefit of priority from Japanese Patent Application No. 2014-108501, filed May 26, 2014, the entire contents of which are incorporated herein by reference.

FIELD

Embodiments described herein relate generally to a pressure sensor, microphone, ultrasonic sensor, blood pressure sensor, and touch panel.

BACKGROUND

Pressure sensors based on the MEMS (Micro Electro Mechanical Systems) technique include a piezoelectric sensor, piezoresistive sensor, capacitance sensor, and the like. On the other hand, a pressure sensor using the spin technique whose sensing principle is different from that of the above-described pressure sensors has been proposed. In the pressure sensor using the spin technique, a spin valve magnetostrictive element (also called a magnetoresistive (MR) element) detects a resistance change corresponding to an anisotropic strain caused by an external pressure. Demands have arisen for increasing the sensitivity of the pressure sensor using the spin technique.

BRIEF DESCRIPTION OF THE DRAWINGS

FIG. 4A is a partial sectional view showing the first structure example of a diaphragm shown in FIG. 2;

FIG. 4B is a partial sectional view showing the second structure example of the diaphragm shown in FIG. 2;

FIG. 4C is a partial sectional view showing the third structure example of the diaphragm shown in FIG. 2;

DETAILED DESCRIPTION

Figure 1:
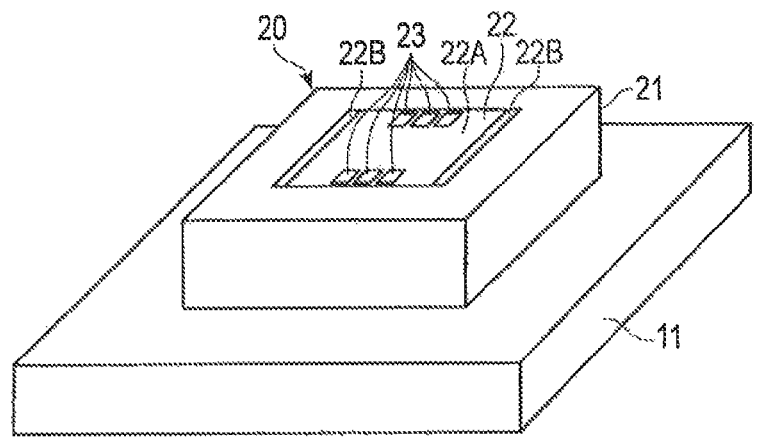
FIG. 1 is a perspective view showing a pressure sensor according to the first embodiment.

According to an embodiment, a pressure sensor includes a support part, a flexible membrane part, and a magnetoresistive element. The flexible membrane part is supported by the support part, and includes a first region and a second region with rigidity lower than rigidity of the first region. The magnetoresistive element is provided on the membrane part, and includes a first magnetic layer, a second magnetic layer, and a spacer layer provided between the first magnetic layer and the second magnetic layer.

Embodiments will be described hereinafter with reference to the accompanying drawings. The embodiments are directed to a pressure sensor based on the MEMS (Micro Electro Mechanical Systems) technique, and a microphone, ultrasonic sensor, blood pressure sensor, and touch panel using the pressure sensor. Note that the drawings are schematic or conceptual, so the relationship between the thickness and width of each part, the size ratio between parts, and the like are not necessarily the same as real ones. Also, the dimension or ratio of even the same part may change from one drawing to another. In the following embodiments, the same reference numerals denote the same elements, and a repetitive explanation thereof will be omitted.

First Embodiment

Figure 2:
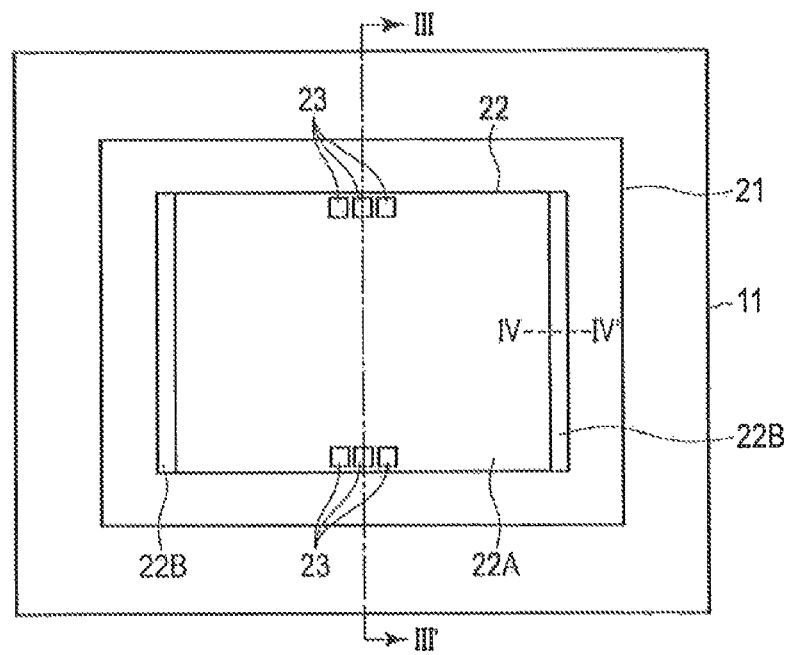
FIG. 2 is a plan view showing the pressure sensor according to the first embodiment.
Figure 3:
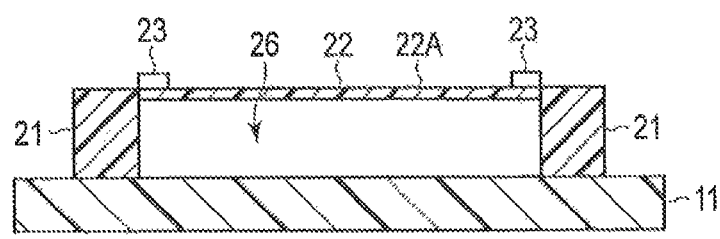
FIG. 3 is a sectional view of the pressure sensor according to the first embodiment.

FIGS. 1 and 2 are respectively a perspective view and plan view schematically showing a pressure sensor according to the first embodiment. FIG. 3 schematically shows a cross-section of the pressure sensor obtained along a line III-III' shown in FIG. 2. FIGS. 1, 2, and 3 do not illustrate insulating parts, conductive parts, and the like for the sake of simplicity. The pressure sensor shown in FIG. 1 includes a resin substrate 11, and a MEMS chip 20 mounted on the resin substrate 11. The MEMS chip 20 is adhered and fixed on the resin substrate 11 by using an adhesive material (also called a die bonding material) such as a thermosetting resin.

The MEMS chip 20 includes a support part 21 provided on the resin substrate 11, a diaphragm 22 corresponding to a flexible membrane part supported by the support part 21, and magnetoresistive elements 23 provided on the diaphragm 22. When an external pressure is applied, the diaphragm 22 bends or warps and applies a strain to the magnetoresistive elements 23 formed on it. The external pressure may be a pressure caused by, for example, pressing, a sound wave, or an ultrasonic wave. The electrical resistance of the magnetoresistive element 23 changes in accordance with the magnitude of the strain having occurred on the magnetoresistive element 23. The pressure sensor according to this embodiment can sense the external pressure by detecting this change in electrical resistance.

Note that FIG. 1 shows an example in which six magnetoresistive elements 23 are provided, but the number of magnetoresistive elements 23 need not be six, and may also be one, two to five, or seven or more.

The support part 21 is, for example, a silicon (Si) substrate. The support part 21 is formed into, for example, a square cylindrical shape having a cavity 26 shown in FIG. 3. The cavity 26 opens to two surfaces of the support part 21 opposing each other. One of these two surfaces is a surface to be adhered to the resin substrate 11, and the diaphragm 22 is fixed to the other of these two surfaces. The cavity 26 is sealed by the resin substrate 11 and the diaphragm 22. The cavity 26 can be filled with a gas such as air or an inert gas, or, on the contrary, can be evacuated. The cavity 26 may also be filled with a liquid. Note that the shape of the support part 21 is not limited to the above-described shape and may also be any arbitrary shape, as long as the support part 21 can support the diaphragm 22 so that the diaphragm 22 can bend when an external pressure is applied. The diaphragm 22 is formed by a thin film such as an amorphous silicon (a-Si) film, silicon oxide ($SiO_x$) film, aluminum oxide ($AlO_x$) film, or silicon nitride (SiN) film. The thin film forming the diaphragm 22 is sometimes continuously formed outside the part which bends due to an external pressure. In this embodiment, that part of the thin film, which bends due to an external pressure, will be called a diaphragm (membrane part). The membrane part is a thin-film region processed to be thin.

The change in electrical resistance of the magnetoresistive element 23 increases as a strain (more specifically, an anisotropic strain as a difference between a maximum principal strain and a minimum principal strain) having occurred on the magnetoresistive element 23 increases. Therefore, to increase the sensitivity of the pressure sensor, the diaphragm 22 is formed so as to generate a large strain with respect to an external pressure. That is, to increase the sensitivity of the pressure sensor, the flexural rigidity of the diaphragm 22 is preferably low. For example, a spring constant k of a circular diaphragm is represented by:

$$k = \frac{16}{3} \frac{\pi E h^3}{a^2(1-v^2)} + 4\pi h \sigma \qquad (1)$$

where E is the Young's modulus of the diaphragm, h is the thickness of the diaphragm, a is the diameter of the diaphragm, and v is the Poisson's ratio. Also, σ represents a membrane stress. σ takes a positive value when the membrane stress is a tensile stress, and a negative value when the membrane stress is a compressive stress. According to equation (1), the flexural rigidity of a diaphragm increases when the membrane stress of the diaphragm is a tensile stress, and decreases when the membrane stress is a compressive stress. Accordingly, the membrane stress is reduced in order to increase the sensitivity of the pressure sensor. However, if an excess compressive stress occurs as the membrane stress of a diaphragm, the diaphragm is wrinkled by buckling. In this case, no appropriate strain can be further applied to the magnetoresistive element formed on the diaphragm.

In the pressure sensor according to this embodiment and those according to other embodiments (to be described later), a low-rigidity region is formed in part of the diaphragm 22. Specifically, as shown in FIG. 2, the diaphragm 22 includes a first region 22A, and second regions 22B having rigidity lower than that of the first region 22A. The second regions 22B are the low-rigidity regions. In this embodiment and the other embodiments (to be described later), the compressive stress occurring on the diaphragm 22 is partially relaxed because the low-rigidity region is formed in part of the diaphragm 22. This makes it possible to suppress the formation of wrinkles on the diaphragm 22. As a consequence, it is possible to further reduce the membrane stress of the diaphragm 22 in order to increase the sensitivity of the pressure sensor.

In this embodiment, the diaphragm 22 is formed into a rectangular shape, the second regions 22B are positioned in the two end parts along the short sides, and the first region 22A is sandwiched between the second regions 22B. The first region 22A includes the two end parts along the long sides of the diaphragm 22 and the central part of the diaphragm 22. The magnetoresistive elements 23 are formed on parts of the first region 22A. That is, the positions of the magnetoresistive element 23 are different from the positions of the second regions 22B as the low-rigidity regions. In the example shown in FIG. 2, three magnetoresistive elements 23 are arranged in each of the two end parts along the long sides. The edges (the two long sides and two short sides) of the diaphragm 22 are fixed to the support part 21. In the rectangular diaphragm 22, an anisotropic strain larger than those in the end parts along the short sides and in the central part occurs in the end parts along the long sides. Therefore, the magnetoresistive elements 23 are preferably arranged in the end parts along the long sides of the diaphragm 22.

Structure examples of the diaphragm 22 according to this embodiment will be explained with reference to FIGS. 4A, 4B, and 4C.

FIG. 4A is a partial sectional view of the pressure sensor taken along a line IV-IV' shown in FIG. 2, and schematically shows the first structure example of the diaphragm 22. In the first structure example shown in FIG. 4A, the thickness of the second region 22B is smaller than that of the first region 22A. That is, the diaphragm 22 is formed so as to be thinner in the second region 22B than in the first region 22A. FIG. 4B is a partial sectional view of the pressure sensor taken along the line IV-IV' shown in FIG. 2, and schematically shows the second structure example of the diaphragm 22. In the second structure example shown in FIG. 4B, the diaphragm 22 is formed flat in the first region 22A, and corrugated in the second region 22B. FIG. 4C is a partial sectional view of the pressure sensor taken along the line IV-IV' shown in FIG. 2, and schematically shows the third structure example of the diaphragm 22. In the third structure example shown in FIG. 4C, the Young's modulus of the second region 22B is lower than that of the first region 22A. Specifically, the second region 22B is formed by a material having a Young's modulus lower than that of the material of the first region 22A.

Note that the method of forming the low-rigidity regions on the diaphragm 22 is not limited to the above-described three structure examples, and it is also possible to combine two or more of the three structure examples, or use another structure.

Figure 5:
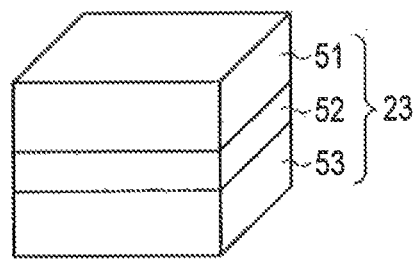
FIG. 5 is a perspective view showing a magnetoresistive element shown in FIG. 1.

FIG. 5 schematically shows one of the six magnetoresistive elements 23 shown in FIG. 1. The remaining five magnetoresistive elements 23 shown in FIG. 1 can have the same structure as that of the magnetoresistive element 23 shown in FIG. 5. FIG. 5 shows a part of the magnetoresistive element 23. As shown in FIG. 5, the magnetoresistive element 23 includes a first magnetic layer 51, a second magnetic layer 53, and an interlayer (also called a spacer layer) 52 arranged between the first magnetic layer 51 and the second magnetic layer 53. At least one of the first magnetic layer 51 and the second magnetic layer 53 is a magnetization free layer in which the magnetization direction is variable. In this embodiment, the first magnetic layer 51 is a magnetization free layer, and the second magnetic layer 53 is a magnetization fixed layer in which the magnetization direction is fixed. The interlayer 52 is a nonmagnetic layer.

An operation by which the magnetoresistive element 23 functions as a strain sensor is based on the application of "the inverse magnetostrictive effect" and "the MR (MagnetoResistance) effect". The inverse magnetostrictive effect is obtained in a ferromagnetic layer to be used as a magnetization free layer. The MR effect appears in a multilayered film in which a magnetization free layer, an interlayer, and a reference layer (e.g., a magnetization fixed layer) are stacked.

The inverse magnetostrictive effect is a phenomenon in which the magnetization direction of a ferromagnetic material changes due to a strain occurring in the ferromagnetic material. That is, when an external strain is applied to the multilayered film of the magnetoresistive element 23, the magnetization direction in the magnetization free layer changes. Consequently, the relative angle between the magnetization directions in the magnetization free layer and the reference layer changes. In this state, the MR effect changes the electrical resistance. The MR effect includes, for example, the GMR (Giant MagnetoResistance) effect or TMR (Tunneling MagnetoResistance) effect. The MR effect appears when an electric current is supplied to the multilayered film. When an electric current is supplied to the multilayered film, a change in relative angle between the magnetization directions can be read as an electrical resistance change. For example, a strain occurs in the multilayered film (the magnetoresistive element 23), the magnetization direction in the magnetization free layer changes due to this strain, and the relative angle between the magnetization directions in the magnetization free layer and reference layer changes. That is, the MR effect appears due to the inverse magnetostrictive effect.

A magnetic layer to be used as the magnetization fixed layer directly contributes to the MR effect. The second magnetic layer 53 as the magnetization fixed layer is made of, for example, a Co—Fe—B alloy. Specifically, a $(Co_xFe_{100-x})_{100-y}B_y$ alloy (x is 0 at. % through 100 at. %, and y is 0 at. % through 30 at. %) can be used as the second magnetic layer 53. As the second magnetic layer 53, another material such as an Fe—Co alloy may also be used.

The interlayer 52 breaks the magnetic bond between the first and second layers 51 and 53. The interlayer 52 is made of, for example, a metal, insulator, or semiconductor. It is possible to use Cu, Au, Ag, etc. as the metal. It is possible to use magnesium oxide (e.g., MgO), aluminum oxide (e.g., $Al_2O_3$), titanium oxide (e.g., TiO), zinc oxide (e.g., ZnO), gallium oxide (Ga—O), etc. as the insulator or semiconductor, it is also possible to use, for example, a CCP (Current-Confined-Path) spacer layer as the interlayer 52. When using the CCP spacer layer as the interlayer 52, it is possible to use, for example, a structure in which a copper (Cu) metal path is formed in an aluminum oxide ($Al_2O_3$) insulating layer.

A ferromagnetic material is used as the first magnetic layer 51 as the magnetization free layer. Specifically, as the material of the first magnetic layer 51, it is possible to use, for example, an alloy containing at least one of Fe and Co, such as an FeCo alloy or NiFe alloy. Alternatively, as the first magnetic layer 51, it is also possible to use, for example, a Co—Fe—B alloy, an Fe—Co—Si—B alloy, an Fe—Ga alloy having a large magnetostrictive constant λs, an Fe—Co—Ga alloy, a Tb-M-Fe alloy, a Tb-M1-Fe-M2 alloy, an Fe-M3-M-B alloy, Ni, Fe—Al, ferrite, etc.

In the pressure sensor according to this embodiment, the diaphragm 22 deforms when an external pressure is applied to it. Accordingly, a strain occurs on the magnetoresistive element 23. In particular, a large anisotropic strain occurs in the end parts along the long sides of the rectangular diaphragm 22 on which the magnetoresistive elements 23 are formed. The large anisotropic strain is a strain having a large difference between a longitudinal-direction strain and widthwise-direction strain, i.e., a large difference between a maximum principal strain and a minimum principal strain. In addition, a larger anisotropic strain can be generated on the magnetoresistive elements 23 by arranging the magnetoresistive elements 23 in the first region 22A different from the low-rigidity regions. Consequently, the sensitivity for sensing an external pressure can be improved.

In the pressure sensor according to the first embodiment as described above, the low-rigidity regions are formed in the two end parts along the short sides of the diaphragm. This makes it possible to reduce the membrane stress of the diaphragm without wrinkling it. As a consequence, the sensitivity for sensing a pressure can be improved.

Second Embodiment

The difference of the second embodiment from the first embodiment is the layout of low-rigidity regions on a diaphragm. Specifically, in the second embodiment, low-rigidity regions are formed in end parts along three sides of a diaphragm formed into a rectangular shape. In the second embodiment, parts different from the first embodiment will be explained, and an explanation of the same parts as those of the first embodiment will be omitted as needed.

Figure 6:
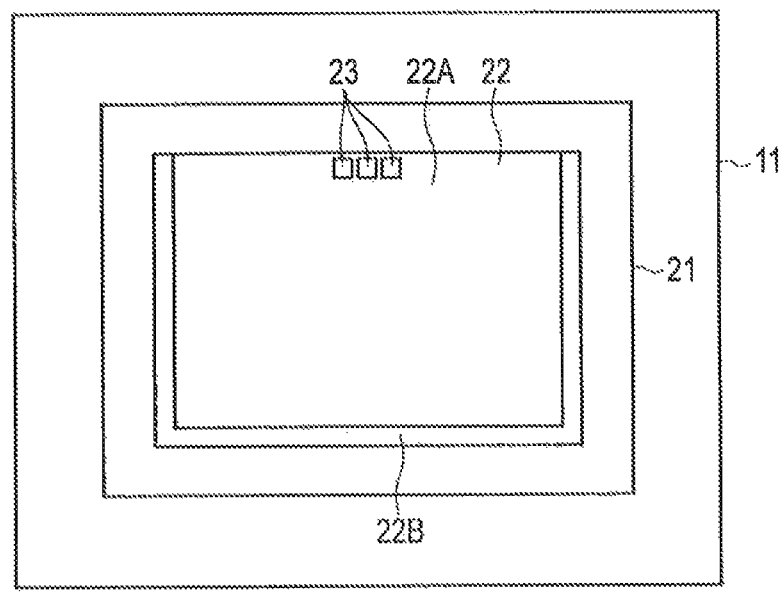
FIG. 6 is a plan view showing a pressure sensor according to the first example of the second embodiment.

FIG. 6 schematically shows a pressure sensor according to the first example of the second embodiment. FIG. 6 does not illustrate insulating parts, conductive parts, and the like for the sake of simplicity. The pressure sensor shown in FIG. 6 includes a resin substrate 11, a support part 21 provided on the resin substrate 11, a flexible diaphragm 22 supported by the support part 21, and at least one magnetoresistive element 23 (in this example, three magnetoresistive elements 23) provided on the diaphragm 22.

The diaphragm 22 includes a first region 22A, and a second region 22B having rigidity lower than that of the first region 22A. In the pressure sensor shown in FIG. 6, the diaphragm 22 is formed into a rectangular shape, and the second region 22B is positioned over the two end parts along the short sides of the diaphragm 22 and one end part along the long side of the diaphragm 22. The magnetoresistive elements 23 are arranged in the other end part along the long side as the first region 22A.

Figure 7:
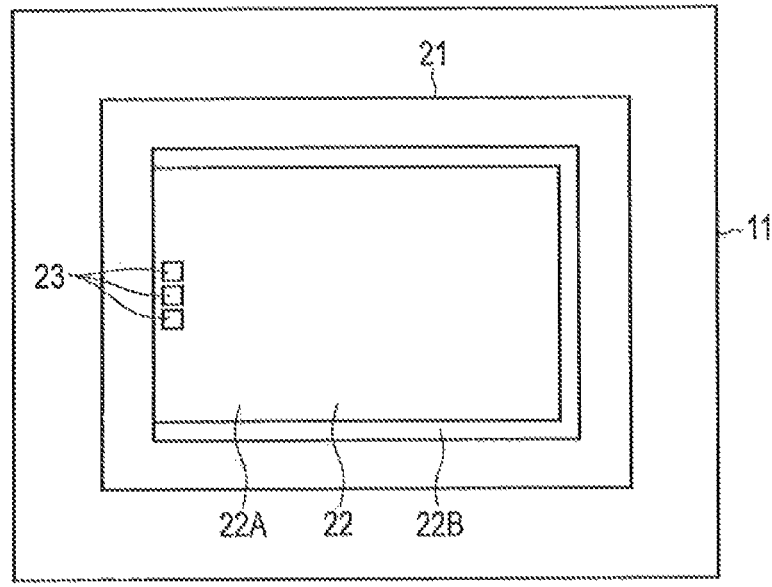
FIG. 7 is a plan view showing a pressure sensor according to the second example of the second embodiment.

FIG. 7 schematically shows a pressure sensor according to the second example of the second embodiment. FIG. 7 does not illustrate insulating parts, conductive parts, and the like for the sake of simplicity. In the pressure sensor shown in FIG. 7, the second region 22B is positioned over the two end parts along the long sides of the diaphragm 22 and one end part along the short side of the diaphragm 22. The magnetoresistive elements 23 are arranged in the other end part along the long side as the first region 22A.

The second embodiment can improve the sensitivity of the pressure sensor as in the first embodiment.

Third Embodiment

The difference of the third embodiment from the first embodiment is the layout of low-rigidity regions on a diaphragm. Specifically, in the third embodiment, a low-rigidity region is formed in the central part of a diaphragm formed into a rectangular shape. In the third embodiment, parts different from the first embodiment will be explained, and an explanation of the same parts as those of the first embodiment will be omitted as needed.

Figure 8:
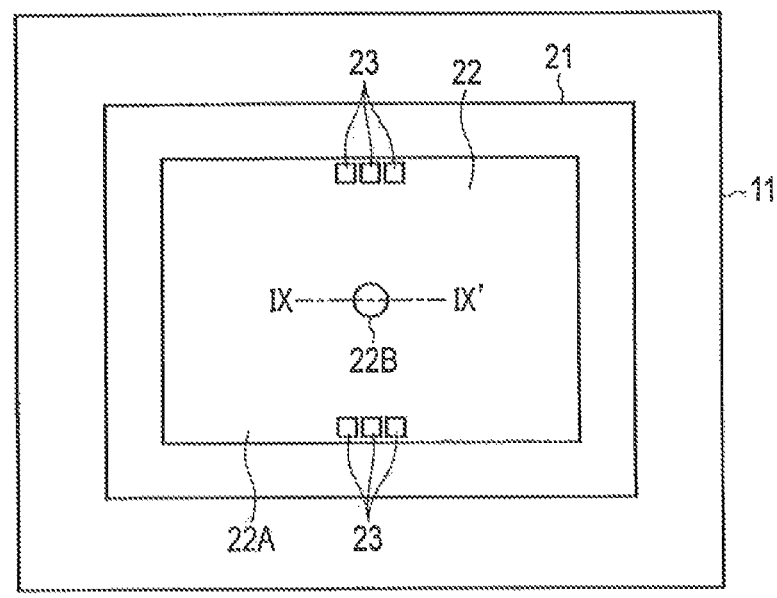
FIG. 8 is a plan view showing a pressure sensor according to the third embodiment.

FIG. 8 schematically shows a pressure sensor according to the third embodiment. FIG. 8 does not illustrate insulating parts, conductive parts, and the like for the sake of simplicity. The pressure sensor shown in FIG. 8 includes a resin substrate 11, a support part 21 provided on the resin substrate 11, a flexible diaphragm 22 supported by the support part 21, and at least one magnetoresistive element 23 (in this example, six magnetoresistive elements 23) provided on the diaphragm 22.

The diaphragm 22 includes a first region 22A, and a second region 22B having rigidity lower than that of the first region 22A. In this embodiment, the second region 22B is positioned in the central part of the diaphragm 22, and has a circular shape. Three magnetoresistive elements 23 are arranged in each of the two end parts along the long sides as the first region 22A.

Figure 9A:
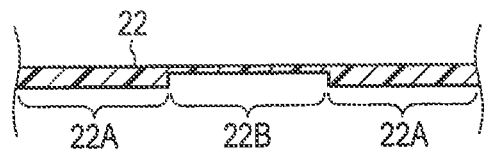
FIG. 9A is a partial sectional view showing the first structure example of a diaphragm shown in FIG. 8.
Figure 9B:
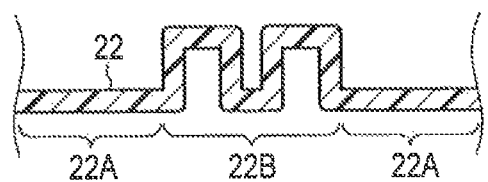
FIG. 9B is a partial sectional view showing the second structure example of the diaphragm shown in FIG. 8.
Figure 9C:
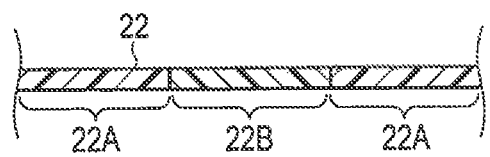
FIG. 9C is a partial sectional view showing the third structure example of the diaphragm shown in FIG. 8.

FIG. 9A is a partial sectional view of the pressure sensor taken along a line IX-IX' shown in FIG. 8, and schematically shows the first structure example of the diaphragm 22. In the first structure example shown in FIG. 9A, the thickness of the second region 22B is smaller than that of the first region 22A. FIG. 9B is a partial sectional view of the pressure sensor taken along the line IX-IX' shown in FIG. 8, and schematically shows the second structure example of the diaphragm 22. In the second structure example shown in FIG. 9B, the diaphragm 22 is corrugated in the second region 22B. FIG. 9C is a partial sectional view of the pressure sensor taken along the line IX-IX' shown in FIG. 8, and schematically shows the third structure example of the diaphragm 22. In the third structure example shown in FIG. 9C, the Young's modulus of the second region 22B is lower than that of the first region 22A.

The third embodiment can improve the sensitivity of the pressure sensor as in the first embodiment.

Fourth Embodiment

The difference of the fourth embodiment from the first embodiment is the layout of low-rigidity regions on a diaphragm. Specifically, the fourth embodiment is a combination of the first and third embodiments, in other words, low-rigidity regions are formed in the two end parts along the short sides of a diaphragm formed into a rectangular shape and in the central part of the diaphragm. In the fourth embodiment, parts different from the first embodiment will be explained, and an explanation of the same parts as those of the first embodiment will be omitted as needed.

Figure 10:
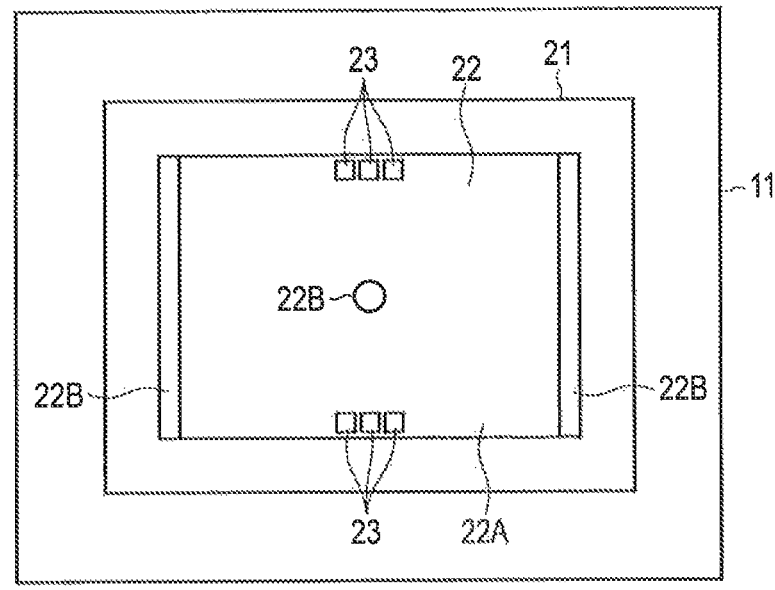
FIG. 10 is a plan view showing a pressure sensor according to the fourth embodiment.

FIG. 10 schematically shows a pressure sensor according to the fourth embodiment. FIG. 10 does not illustrate insulating parts, conductive parts, and the like for the sake of simplicity. The pressure sensor shown in FIG. 10 includes a resin substrate 11, a support part 21 provided on the resin substrate 11, a flexible diaphragm 22 supported by the support part 21, and at least one magnetoresistive element 23 (in this example, six magnetoresistive elements 23) provided on the diaphragm 22.

The diaphragm 22 includes a first region 22A, and second regions 22B having rigidity lower than that of the first region 22A. In this embodiment, the second regions 22B are positioned in the two end parts along the short sides and in the central part of the diaphragm 22. Three magnetoresistive elements 23 are arranged in each of the two end parts along the long sides as the first region 22A.

The fourth embodiment can improve the sensitivity of the pressure sensor as in the first embodiment.

Fifth Embodiment

The differences of the fifth embodiment from the first embodiment are the shape of a diaphragm and the layout of magnetoresistive elements. Specifically, the diaphragm is formed into a circular shape in the fifth embodiment. In the fifth embodiment, parts different from the first embodiment will be explained, and an explanation of the same parts as those of the first embodiment will be omitted as needed.

Figure 11:
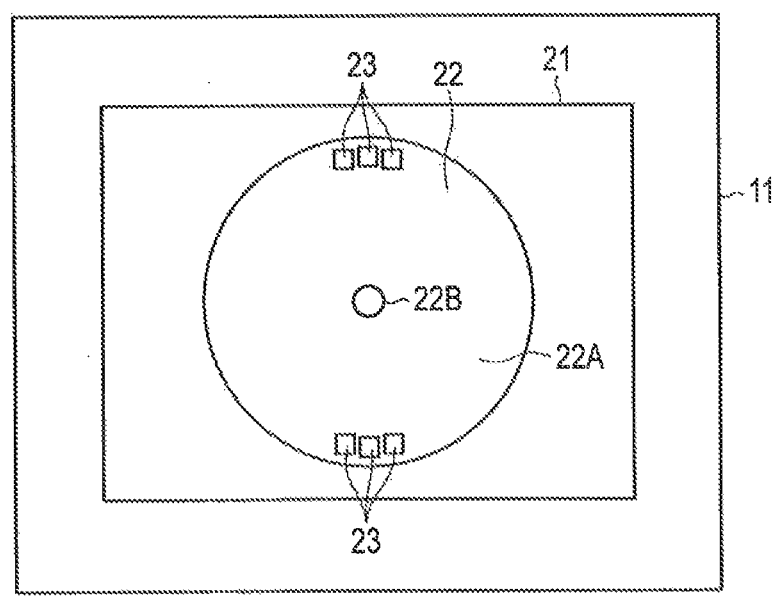
FIG. 11 is a plan view showing a pressure sensor according to the fifth embodiment.

FIG. 11 schematically shows a pressure sensor according to the fifth embodiment. FIG. 11 does not illustrate insulating parts, conductive parts, and the like for the sake of simplicity. The pressure sensor shown in FIG. 11 includes a resin substrate 11, a support part 21 provided on the resin substrate 11, a flexible diaphragm 22 supported by the support part 21, and at least one magnetoresistive element 23 (in this example, six magnetoresistive elements 23) provided on the diaphragm 22.

The diaphragm 22 includes a first region 22A, and a second region 22B having rigidity lower than that of the first region 22A. In this embodiment, the second region 22B is a circular region, and positioned in the central part of the diaphragm 22. The magnetoresistive elements 23 are arranged along the periphery of the diaphragm 22. Specifically, three magnetoresistive elements 23 are arranged in each of two end parts opposing each other with the second region 22B being interposed between them.

The fifth embodiment can improve the sensitivity of the pressure sensor as in the first embodiment.

Sixth Embodiment

The difference of the sixth embodiment from the first embodiment is the shape of a diaphragm. In the sixth embodiment, the diaphragm is formed into a circular shape as in the fifth embodiment, but the layout of low-rigidity regions on the diaphragm differs from that of the fifth embodiment. Specifically, in the sixth embodiment, a low-rigidity region is formed in at least a part of the periphery of the diaphragm formed into a circular shape. In the sixth embodiment, parts different from the first embodiment will be explained, and an explanation of the same parts as those of the first embodiment will be omitted as needed.

Figure 12:
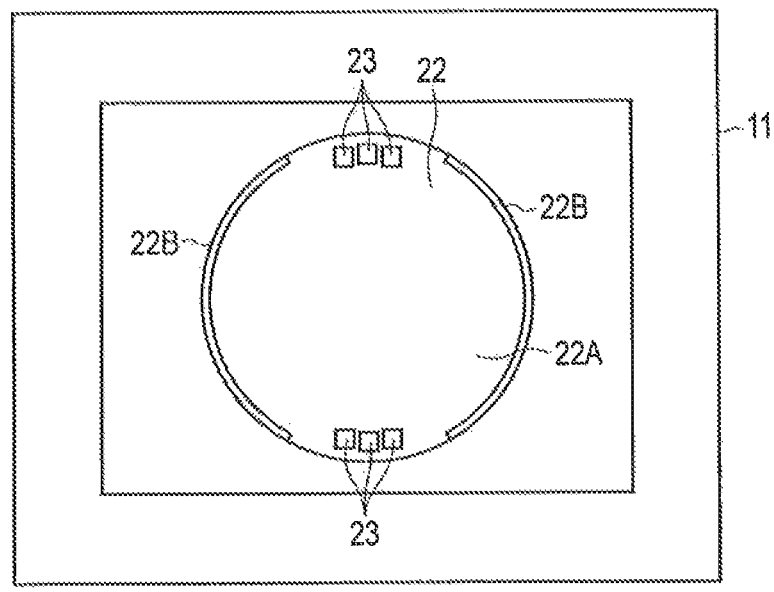
FIG. 12 is a plan view showing a pressure sensor according to the sixth embodiment.

FIG. 12 schematically shows a pressure sensor according to the sixth embodiment, FIG. 12 does not illustrate insulating parts, conductive parts, and the like for the sake of simplicity. The pressure sensor shown in FIG. 12 includes a resin substrate 11, a support part 21 provided on the resin substrate 11, a flexible diaphragm 22 supported by the support part 21, and at least one magnetoresistive element 23 (in this example, six magnetoresistive elements 23) provided on the diaphragm 22.

The diaphragm 22 includes a first region 22A, and second regions 22B having rigidity lower than that of the first region 22A. In this embodiment, the second regions 22B are positioned in two parts of the periphery of the diaphragm 22. These two parts oppose each other with the center of the diaphragm 22 being interposed between them. The magnetoresistive elements 23 are arranged along the periphery of the diaphragm 22 on the first region 22A. Specifically, three magnetoresistive elements 23 are arranged in each of two parts of the periphery of the diaphragm 22, which are different from the second regions 22B. The periphery of the diaphragm 22 includes the two parts of the second regions 22B, and the two parts of the first region 22A positioned between the former two parts.

The sixth embodiment can improve the sensitivity of the pressure sensor as in the first embodiment.

Seventh Embodiment

The difference of the seventh embodiment from the first embodiment is the shape of a diaphragm. The seventh embodiment is a combination of the fifth and sixth embodiments, and low-rigidity regions are formed in the central part of a diaphragm formed into a circular shape, and in at least a part of the periphery of the diaphragm. In the seventh embodiment, parts different from the first embodiment will be explained, and an explanation of the same parts as those of the first embodiment will be omitted as needed.

Figure 13:
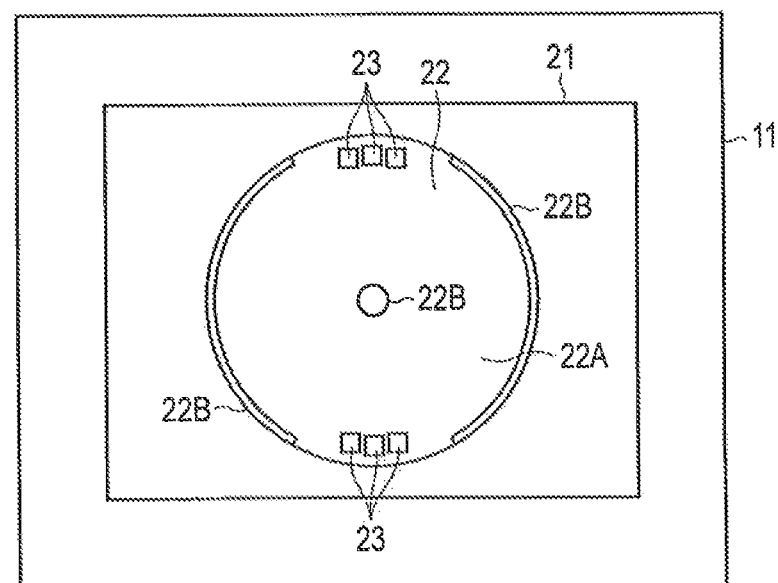
FIG. 13 is a plan view showing a pressure sensor according to the seventh embodiment.

FIG. 13 schematically shows a pressure sensor according to the seventh embodiment. FIG. 13 does not illustrate insulating parts, conductive parts, and the like for the sake of simplicity. The pressure sensor shown in FIG. 13 includes a resin substrate 11, a support part 21 provided on the resin substrate 11, a flexible diaphragm 22 supported by the support part 21, and at least one magnetoresistive element 23 (in this example, six magnetoresistive elements 23) provided on the diaphragm 22.

The diaphragm 22 includes a first region 22A, and second regions 22B having rigidity lower than that of the first region 22A. In this embodiment, the second regions 22B are positioned in the central part and in two parts of the periphery of the diaphragm 22. These two parts oppose each other with the central part of the diaphragm 22 being interposed between them. Three magnetoresistive elements 23 are arranged in each of two parts of the periphery of the diaphragm 22, which are different from the second regions 22B.

The seventh embodiment can improve the sensitivity of the pressure sensor as in the first embodiment.

Note that the planar shape of the diaphragm 22 is not limited to the shapes (a rectangle and circle) exemplified in the first to seventh embodiments, and may also be another shape such as an ellipse. In addition, the positions of the second regions (low-rigidity regions) 22B and the layout of the magnetoresistive elements 23 on the diaphragm 22 are not limited to those explained in the first to seventh embodiments, and may also be changed as needed. Also, the shape of the second region (low-rigidity region) 22B on the diaphragm 22 is not limited to a circle exemplified in the embodiments, and may also be, for example, a square, rectangle, or ellipse. Furthermore, the substrate on which the MEMS chip 20 is mounted is not limited to a resin substrate, and may also be a ceramic substrate or the like.

Eighth Embodiment

Figure 14:
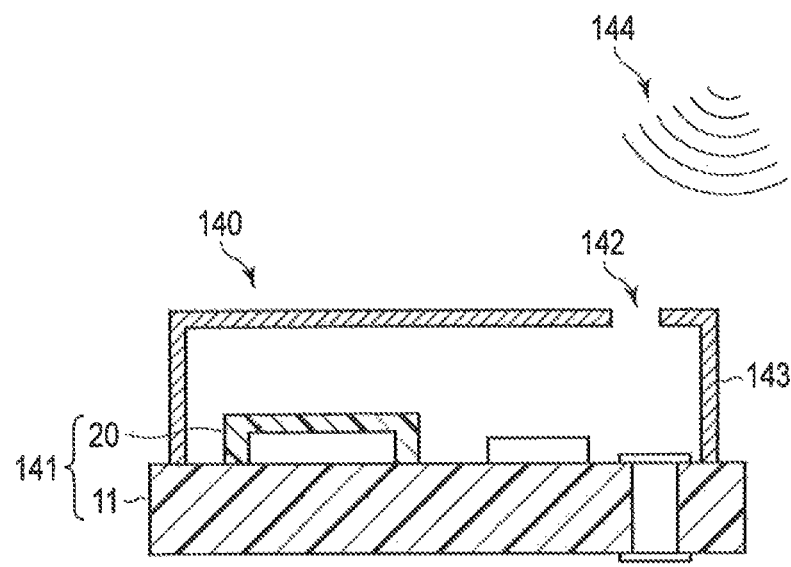
FIG. 14 is a sectional view showing a microphone according to the eighth embodiment.

FIG. 14 schematically shows a microphone 140 according to the eighth embodiment. The microphone 140 includes a pressure sensor 141. The pressure sensor 141 can be one of the pressure sensors explained in the first to seventh embodiments, or a modification thereof. The pressure sensor 141 of this embodiment is the pressure sensor according to the first embodiment.

The pressure sensor 141 includes a resin substrate 11, and a MEMS chip 20 mounted on the resin substrate 11. The resin substrate 11 includes a circuit such as an amplifier. A cover 143 is formed on the resin substrate 11 so as to cover the MEMS chip 20. An opening 142 is formed in the cover 143. A sound wave 144 propagates inside the cover 143 through the opening 142.

The microphone 140 is sensitive to the sound pressure of the sound wave 144. The microphone 140 having high sensitivity to frequencies in a broad range can be obtained by using a high-sensitivity pressure sensor. As a method of reducing a compressive stress occurring on a diaphragm, a method of forming a slit or through hole in the diaphragm is possible. When using a pressure sensor in a microphone, however, the slit or through hole causes roll-off in a low-frequency region by a wraparound of sound waves. In the pressure sensor 141 of this embodiment, this roll-off by a wraparound of sound waves does not occur, so the sensitivity is high in a low-frequency region as well.

Note that the sound wave 144 is not limited to an audible-range signal and may also be an ultrasonic wave. When designing the diaphragm 22 so that the resonance frequency of the diaphragm 22 is the frequency band of an ultrasonic wave, the microphone 140 can function as an ultrasonic sensor. More preferably, the opening 142 is formed immediately above the diaphragm (not shown in FIG. 14) of the pressure sensor 141, or formed in the resin substrate 11 immediately below the diaphragm, because the ability of the sound wave 144 to travel straight increases when it is an ultrasonic wave. Furthermore, a dust-proof mesh is desirably formed in the opening 142.

Figure 15:
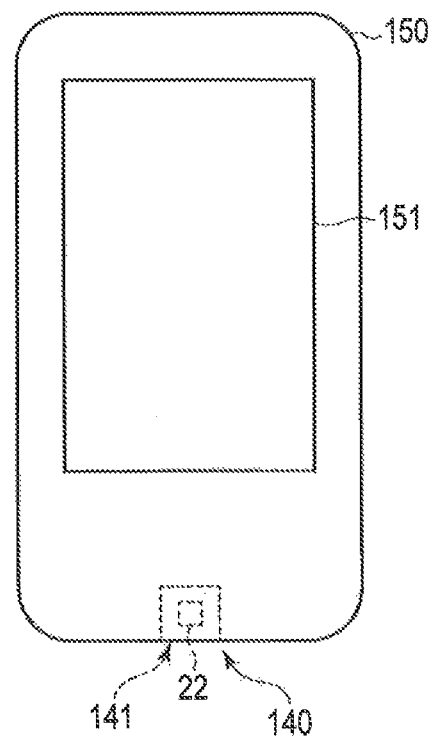
FIG. 15 is a front view showing a personal digital assistance including the microphone shown in FIG. 14.

FIG. 15 schematically shows an example in which the microphone 140 is applied to a personal digital assistance 150. As shown in FIG. 15, the microphone 140 is provided on the end part of the personal digital assistance 150. For example, the microphone 140 is arranged so that the diaphragm 22 of the pressure sensor 141 is practically parallel to the surface of the personal digital assistance 150, on which a display 151 is formed. Note that the position of the diaphragm 22 is not limited to the example shown in FIG. 14, and can be changed as needed.

Note also that the microphone 140 can be applied not only to the personal digital assistance 150 as shown in FIG. 15, but also to an IC recorder, pin microphone, or the like.

Ninth Embodiment

Figure 16:
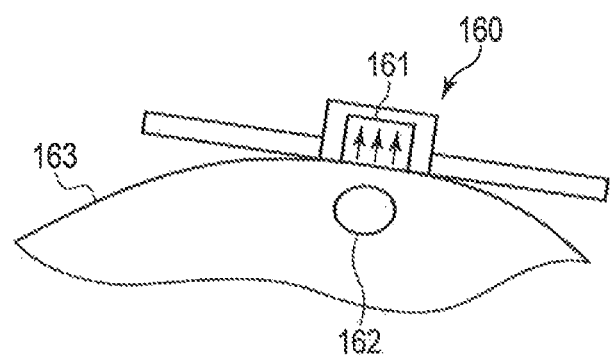
FIG. 16 is a sectional view showing a blood pressure sensor according to the ninth embodiment.

FIG. 16 schematically shows a blood pressure sensor 160 according to the ninth embodiment. The blood pressure sensor 160 shown in FIG. 16 measures a persons blood pressure, and includes a pressure sensor 161. The pressure sensor 161 can be one of the pressure sensors explained in the first to seventh embodiments, or a modification thereof. The pressure sensor 161 of this embodiment is the pressure sensor according to the first embodiment, and is capable of high-sensitivity pressure sensing with a small size.

The blood pressure sensor 160 can continuously perform blood pressure measurement by pressing the pressure sensor 161 against a skin 163 on an artery 162. This embodiment provides the blood pressure sensor 160 having high sensitivity.

10th Embodiment

Figure 17:
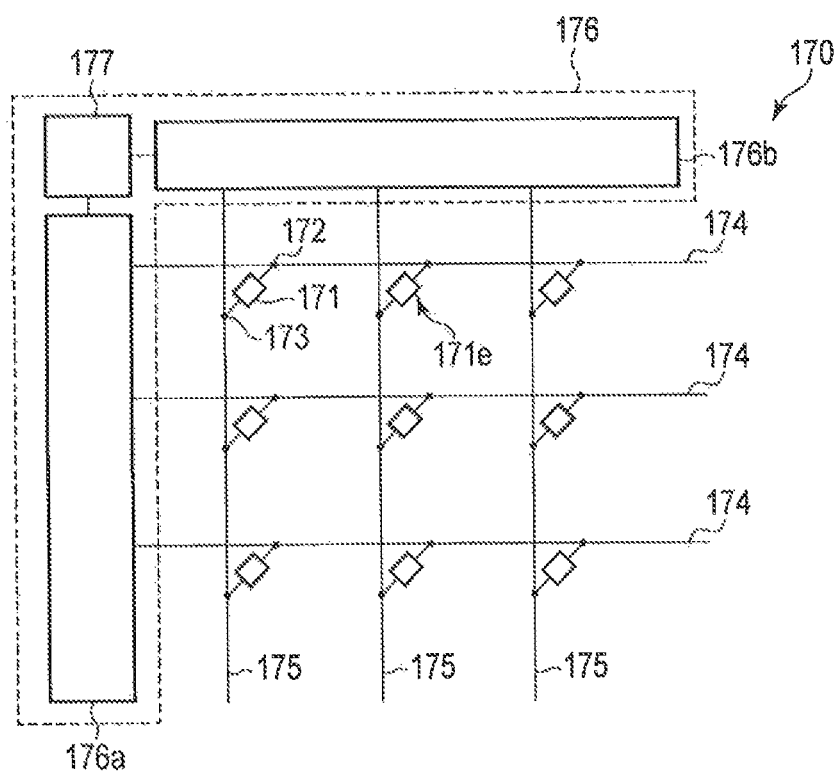
FIG. 17 is a block diagram showing a touch panel according to the 10th embodiment.

FIG. 17 schematically shows a touch panel 170 according to the 10th embodiment. As shown in FIG. 17, the touch panel 170 includes first lines 174, second lines 175, pressure sensors 171, and a controller 176. Each of the pressure sensors 171 can be one of the pressure sensors according to the first to seventh embodiments, or a modification thereof.

The pressure sensors 171 are mounted inside or outside a display.

The first lines 174 are arranged along a first direction. Each of the first lines 174 runs along a second direction perpendicular to the first direction. The second lines 175 are arranged along the second direction. Each of the second lines 175 runs along the first direction.

Each of the pressure sensors 171 is formed in each of the intersections of the first lines 174 and the second lines 175. Each pressure sensor 171 functions as a detection element 171e for detection. The intersection herein mentioned includes a position where the first and second lines 174 and 175 intersect, and a peripheral region thereof.

An end 172 of each of the pressure sensors 171 is connected to a corresponding one of the first lines 174. An end 173 of each of the pressure sensors 171 is connected to a corresponding one of the second lines 175.

The controller 176 is connected to the first lines 174 and the second lines 175. The controller 176 includes a first-line circuit 176a connected to the first lines 174, a second-line circuit 176b connected to the second lines 175, and a control circuit 177 connected to the first-line circuit 176a and second-line circuit 176b.

The pressure sensor 171 is capable of high-sensitivity pressure sensing with a small size. This makes it possible to implement a high-definition touch panel.

The pressure sensors according to the first to seventh embodiments are not limited to the above-mentioned applications, and are also applicable to various pressure sensor devices such as an atmospheric pressure sensor and tire inflation pressure sensor.

According to the embodiments, there are provided a high-sensitivity pressure sensor, microphone, ultrasonic sensor, blood pressure sensor, and touch panel.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A pressure sensor comprising:
    a membrane including a first region and a second region, the second region having rigidity lower than rigidity of the first region, the second region including a first part and a second part, the first region being arranged between the first part and the second part of the second region;
    a support member supporting a part of the membrane, the first part of the second region of the membrane being arranged between the support member and the first region of the membrane, the second part of the second region of the membrane being arranged between the first region of the membrane and the support member; and
    a magnetoresistive element provided on the membrane, the magnetoresistive element including a first magnetic layer, a second magnetic layer, and a spacer layer provided between the first magnetic layer and the second magnetic layer, an electrical resistance of the magnetoresistive element changing in accordance with a strain of the membrane.

2. The sensor according to claim 1, wherein a thickness of the second region is smaller than a thickness of the first region.

3. The sensor according to claim 1, wherein the membrane in the second region is corrugated.

4. The sensor according to claim 1, wherein a Young's modulus of the second region is lower than a Young's modulus of the first region.

5. The sensor according to claim 1, wherein the magnetoresistive element is provided on the first region of the membrane.

6. The sensor according to claim 5, wherein the membrane is formed into a rectangular shape, the first part and the second part of the second region are separated from each other and are positioned in each of end parts along two short sides of the first region of the membrane, and the magnetoresistive element is provided on an end part along a long side of the first region of the membrane.

7. The sensor according to claim 5, wherein the membrane is formed into a rectangular shape, the second region further includes a third part, the first part, the second part, and the third part of the second region are continuous and are positioned in each of end parts along three sides of the first region of the membrane, and the magnetoresistive element is provided on an end part along a remaining side of the first region of the membrane.

8. The sensor according to claim 5, wherein the membrane is formed into a rectangular shape, the second region further includes a third part, the first part, the second part, and the third part of the second region are separated from each other, the first part and the second part of the second region are positioned in each of end parts along two short sides of the first region of the membrane, the third part of the second region is positioned in a central part of the first region of the membrane, and the magnetoresistive element is provided on an end part along a long side of the first region of the membrane.

9. The sensor according to claim 5, wherein the membrane is formed into a circular shape.

10. The sensor according to claim 1, comprising a plurality of magnetoresistive elements provided on the membrane.

11. A microphone comprising the pressure sensor according to claim 1.

12. An ultrasonic sensor comprising the pressure sensor according to claim 1.

13. A blood pressure sensor comprising the pressure sensor according to claim 1.

14. A touch panel comprising the pressure sensor according to claim 1.

15. A sensor comprising:
    a membrane including a first region and a second region, the second region having rigidity lower than rigidity of the first region and including a first part and a second part, the first region of the membrane being arranged between the first part and the second part of the second region of the membrane;
    a support member supporting a part of the membrane, the first part of the second region of the membrane being arranged between the support member and the first region of the membrane, the second part of the second region of the membrane being arranged between the first region of the membrane and the support member;
    a substrate on which the support member is provided;

a magnetoresistive element provided on the membrane, the magnetoresistive element including a first magnetic layer, a second magnetic layer, and a spacer layer provided between the first magnetic layer and the second magnetic layer, an electrical resistance of the magnetoresistive element changing in accordance with a strain of the membrane; and a cover provided on the substrate, the cover and the substrate containing the support member, the membrane and the magnetoresistive element, the cover or the substrate being provided with an opening.

16. A sensor comprising:

a membrane including a first region and a second region, the second region having rigidity lower than rigidity of the first region and including a first part and a second part, the first region of the membrane being arranged between the first part and the second part of the second region of the membrane;

a support member supporting a part of the membrane, the first part of the second region of the membrane being arranged between the support member and the first region of the membrane, the second part of the second region of the membrane being arranged between the first region of the membrane and the support member; and a magnetoresistive element provided on the membrane, the magnetoresistive element including a first magnetic layer, a second magnetic layer, and a spacer layer provided between the first magnetic layer and the second magnetic layer, an electrical resistance of the magnetoresistive element changing in accordance with a strain of the membrane, the strain of the membrane being induced by sound pressure.

* * * * *